(12) United States Patent
Norman et al.

(10) Patent No.: US 6,519,030 B1
(45) Date of Patent: Feb. 11, 2003

(54) FLAME PHOTOMETER DETECTOR

(75) Inventors: Paul R Norman, Salisbury (GB);
George A Robins, Salisbury (GB);
Arthur M Johnston, Edinburgh (GB);
Grant S Richardson, Salisbury (GB)

(73) Assignee: The Secretary of State for Defence in Her Britannic Majesty's Government of the United Kingdom of Great Britain and Northern Ireland, Farnborough (GB)

( * ) Notice: Subject to any disclaimer, the term of this patent is extended or adjusted under 35 U.S.C. 154(b) by 0 days.

(21) Appl. No.: 09/647,178

(22) PCT Filed: Mar. 22, 1999

(86) PCT No.: PCT/GB99/00906

§ 371 (c)(1),
(2), (4) Date: Jan. 2, 2000

(87) PCT Pub. No.: WO99/50649

PCT Pub. Date: Oct. 7, 1999

(30) Foreign Application Priority Data

Mar. 27, 1998 (GB) .............................. 9806555

(51) Int. Cl.[7] .............................. G01J 3/30; G01J 1/00
(52) U.S. Cl. .................... 356/315; 356/307; 356/417; 356/213
(58) Field of Search ............................ 356/417, 213, 356/221, 229, 437, 439, 442, 315, 307

(56) References Cited

U.S. PATENT DOCUMENTS 5,153,673 A * 10/1992 Amirav ..................... 356/315
5,473,162 A * 12/1995 Busch et al. ........... 250/339.08

* cited by examiner

Primary Examiner—Frank G. Font
Assistant Examiner—Roy M. Punnoose
(74) Attorney, Agent, or Firm—Nixon & Vanderhye P.C.

(57) ABSTRACT

A flame photometer detector is described which uses flame emission spectroscopy as the detection method, computer control and data acquisition, pulsed sampling and a rotating reference filter wheel to eliminate the effects of background chemical species. The detector is particularly suited to the testing of respirator equipment.

15 Claims, 4 Drawing Sheets

Inhalation

Exhalation

FLAME PHOTOMETER DETECTOR

BACKGROUND OF THE INVENTION

1. Field of the Invention

The current invention relates to a flame photometer detector having improved sensitivity.

2. Discussion of Prior Art

The analytical technique of flame photometry is well known. Typically, a sample is introduced to a hydrogen flame and electrons in the outer shell of atoms of the substance of interest are excited to a higher state of energy. When the electron returns to its ground state, energy is emitted in the form of light by which the presence of the substance is confirmed.

The wavelength of the emitted light depends on the substance of interest. Typically the light is detected using a photomultiplier tube (PMT) which provides a quantitative analysis of sample present. An optical filter having a narrow passband centred on the wavelength associated with the substance affords selectivity.

One application in which flame photometers are used is the testing of military respirators.

The effectiveness of the respirator in providing protection against a particular agent is expressed as the protection factor (PF). This is the ratio of the concentration of agent outside the respirator to that found within. The concentration within results from a combination of the various leak paths, namely the face seal, the outlet valve and the filter.

One method of testing respirator leakage involves measuring the penetration of solid salt (sodium chloride) aerosol using flame emission spectroscopy as the detection method. A subject wearing a respirator under test is placed in a test chamber into which the aerosol (typically of concentration 13 mg m$^{-3}$) is introduced. The aerosol is produced using a Collison atomiser to aspirate a salt solution into droplets. These are diluted to the required concentration and dried using a fan to produce the solid aerosol which enters the test chamber. The solid aerosol so produced has a mean diameter $0.6 \times 10^{-6}$ m but the particle sizes range from $0.05 \times 10^{-6}$ m to $1.2 \times 10^{-6}$ m. During testing a continuous sample is drawn from inside the face mask of the respirator into the flame chamber of the photometer.

On entering the flame, the salt gives rise to radiation having a wavelength of 598.6 nm. This passes through a narrow pass filter, which inhibits transmission of other light. When measuring high salt concentrations, neutral density (ND) filters are introduced to prevent flooding of the photomultiplier. These filters reduce the intensity of light reaching the photomultiplier by a calibrated amount.

The response from the photomultiplier is recorded on, for example, a chart recorder and the effect of any ND filters is taken into account in the following expression for calculating salt concentration:

total deflection due to salt=antilog ND value (salt signal)−clean air signal

This deflection value is then used to obtain the percentage penetration calculated from a calibration curve produced specifically for that instrument. A penetration of 0.01% is equivalent to a PF of $10^4$.

A typical limit of detection of devices currently in use is about 20 ng m$^{-3}$. For the test procedure described above, this corresponds to a PF of $6.5 \times 10^5$.

The current requirement for the PF of high efficiency military respirators is $10^4$ but this likely to be significantly increased, due to the increased demands of the modern battlefield environment.

Thus, in addition to the general benefit to the art of flame photometry afforded by a device which offers improved detection limits, there is a specific requirement, for the testing of high efficiency military respirators.

Another problem encountered during the testing of respirators is that of lung retention: continuously sampling air from the inside of the mask (during both inhalation and exhalation) means that observed results are affected by retention of salt by the lungs.

At present, this is accounted for by exposing the challenge aerosol to lung retention at the end of the respirator test and deriving a lung retention factor which is incorporated in the calculation of percentage penetration. This method is not seen as ideal because it may not be appropriate to use the lung retention factor measured for the neat cloud for calculations involving exposure to low concentrations of salt inside the respirator during test. A typical analysis from the output of a Collison atomiser (based on a 2% w/v solution of NaCl in water and a 12.5 Lmin$^{-1}$ flow through the saline solution diluted to 90 Lmin$^{-1}$ with atmospheric air) shows a solid NaCl concentration of ~13 mgm$^{-3}$. This enables an estimate of the detection limits required at a PF of $10^6$.

SUMMARY OF THE INVENTION

According to the present invention a flame photometer detector comprises:

a flame chamber having a burner, a hydrogen inlet, a sample inlet and a window, transparent to radiation produced therein;

means for detecting independently a first radiation and a second radiation, and producing corresponding electrical signals, wherein the intensity of the first radiation is dependent on the concentration in the flame chamber of at least one chemical species to be detected and of one or more background chemical species and the intensity of the second radiation is substantially independent of the concentration in the flame chamber of the chemical species to be detected and is dependent on the concentration in the flame chamber of the background chemicals species and data acquisition means for measuring the electrical signals and comparing the data so obtained with calibration data obtained in the presence of the background chemical species and the absence of the chemical species to be detected.

Preferably the data acquisition means is capable of acquiring data at a rate sufficient to record single particle events within the flame chamber.

A further preferred embodiment includes means for modulating the first and second radiation, the detecting means being selective to radiation so modulated.

A further preferred embodiment includes means for directing radiation exiting the flame chamber on to the filters and, or means for directing modulated radiation towards the means for detecting radiation. Such means for directing radiation might comprise a lens.

The detecting means comprises a photomultiplier tube.

In a particular embodiment the detector is used in testing the efficiency of respirators, and further comprising means for directing sample air from the interior of a respirator to the flame chamber during inhalation by a subject wearing said facemask. Means might also be included for directing fresh air to the interior of the respirator during exhalation.

According to a second aspect of the invention, a method of measuring the presence of a chemical species using a flame photometer detector includses the steps of:

i) measuring a first radiation and a second radiation, and producing corresponding electrical signals, wherein the intensity of the first radiation is dependent on the concentration in the flame chamber of the chemical species to be detected and of one or more background chemical species and the intensity of the second radiation is substantially independent of the concentration in the flame chamber of the chemical species to be detected and is dependent on the concentration in the flame chamber of the background chemicals species and ii) comparing the data so obtained with calibration data obtained in the presence of the background chemical species and the absence of the chemical species to be detected.

BRIEF DESCRIPTION OF THE DRAWINGS

The invention will now be described with reference to the following figures in which.

DETAILED DISCUSSION OF EMBODIMENTS

Figure 1:
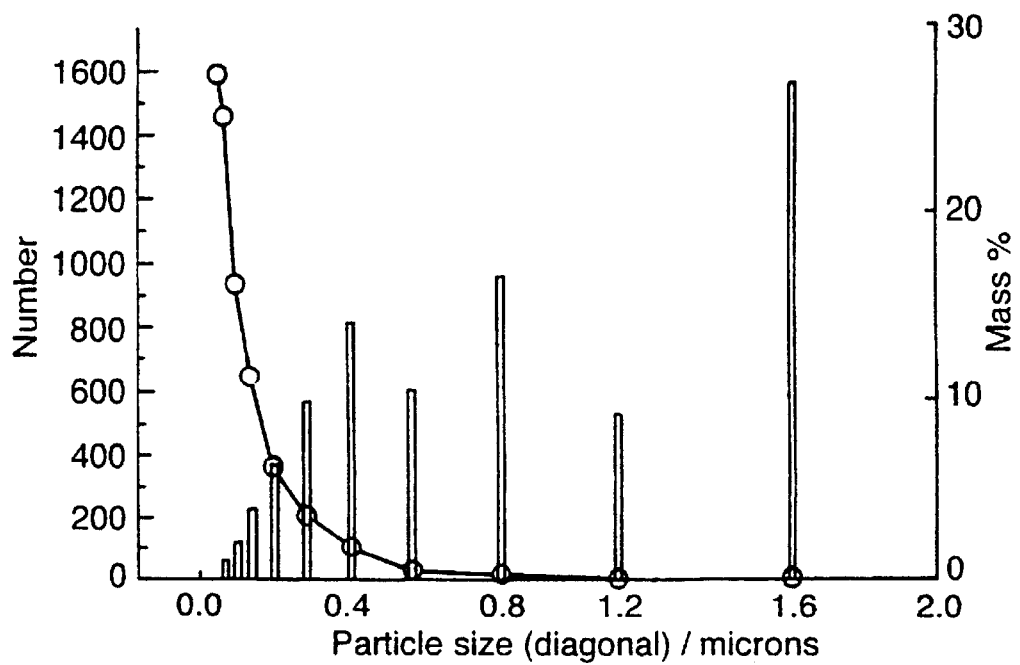
FIG. 1 shows a typical analysis of the output of a Collison atomiser.

FIG. 1 shows a typical number and size distribution that might be expected in one 2 L breath sample a PF of $10^6$. The anticipated NaCl concentration will be 13 ng $m^{-3}$ but, perhaps more importantly, the distribution becomes critical: over 50% of the mass is contained in a few tens of particles. The apparatus therefore needs to be able to detect individual salt particles and this need necessitates a stable background and interference correction.

Figure 2:
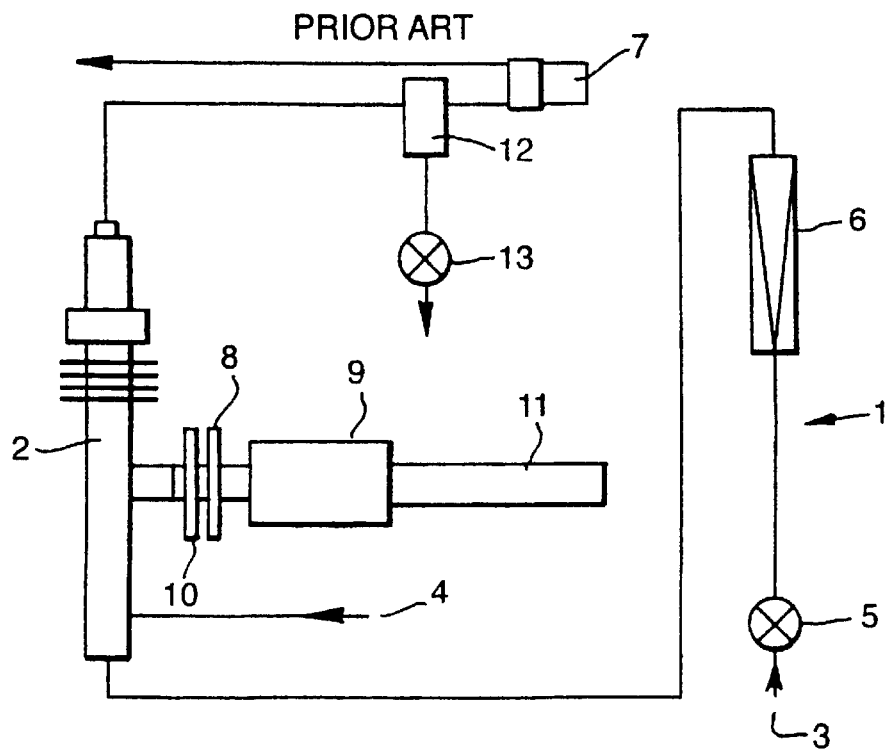
FIG. 2 shows a flame photometer of the prior art.

Referring to FIG. 2 a typical low flow luminometer of the prior art (generally designated 1) includes a flame chamber 2, into which hydrogen gas and sample air enter via inlets 3 and 4 respectively.

The flow of hydrogen, from a positive pressure source (not shown) is regulated by valve 5 to approximately 0.5 l $min^{-1}$ and may be monitored by means of flowmeter 6. The flow of sample air to the flame is maintained by vacuum pump and a critical orifice (not shown) at the exit from flame chamber 2. The instrument may include means for diluting the sample air before directing a fraction thereof to the flame.

Light emitted from the flame is passed through a narrow band pass filter 8, having a bandwidth of 3 nm centred on the sodium "D" lines, to a photomultiplier 9 where a corresponding current signal is produced. A neutral density filter 10 is also included to protect the photomultiplier 9 from high levels of light. After amplification, the signal is displayed on an analogue panel meter 11.

An external signal output (not shown) is also typically provided for connection to e.g. a chart recorder.

Pump 7 is protected by a vacuum filter 12 which may be drained via valve 13.

Figure 3:
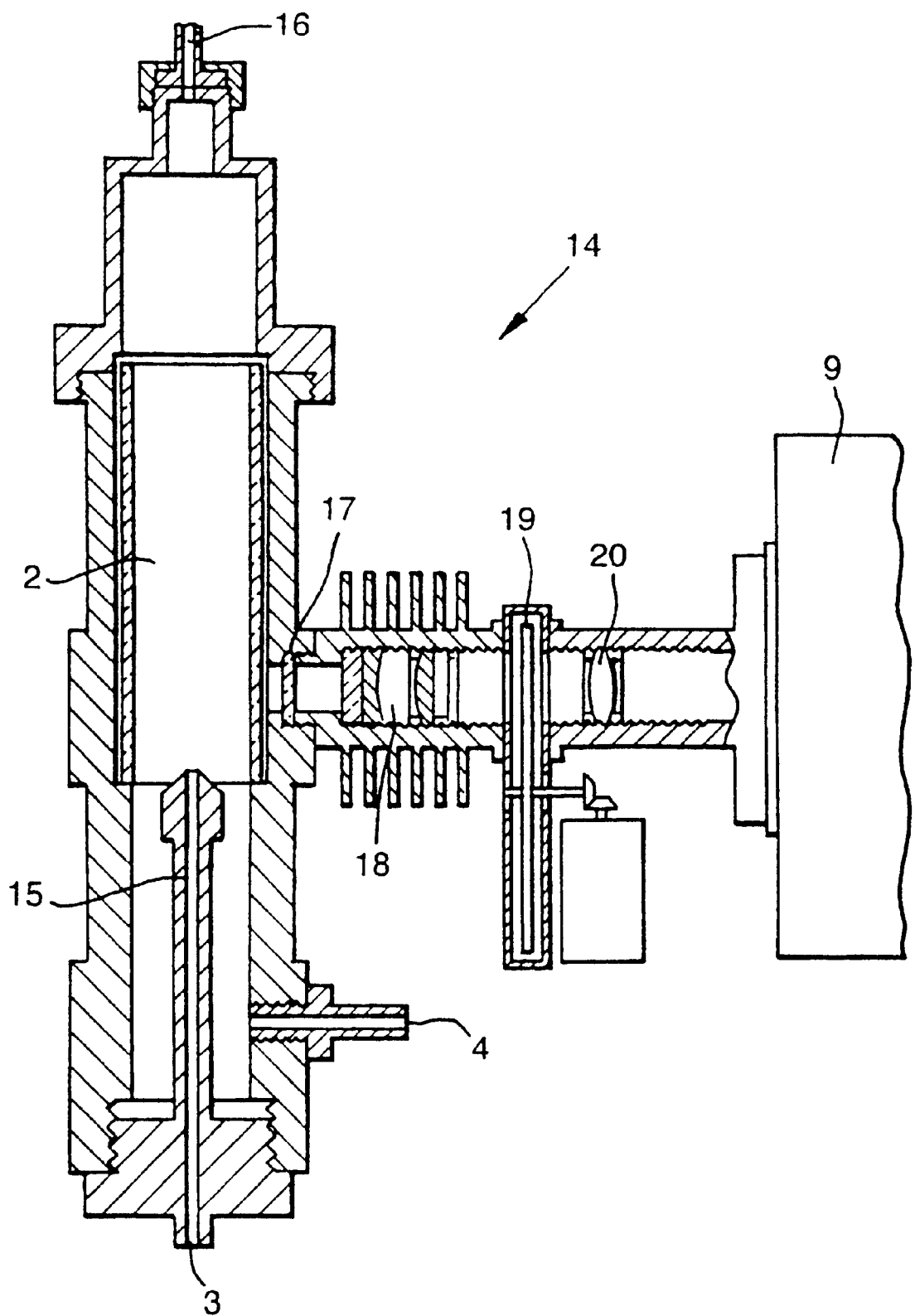
FIG. 3 shows a flame photometer of the current invention.

Referring to FIG. 3 the improved flame photometer of the current invention (generally designated 14) includes a flame chamber 2 having a hydrogen inlet 3, a sample inlet 4 and a burner 15. Outlet 16 leads to a sampling pump (not shown) incorporating a critical orifice which maintains a sample flow of 2 l $min^{-1}$. The pump is protected by a trap (not shown) which collects the water produced by the combustion of hydrogen. The external design of the flame chamber includes cooling fins (not shown).

A quartz window 17 is located in the wall of the flame chamber 2 and this facilitates transmission of light from the flame to a pair of condensing lenses 18 which focus the beam through a slit (not shown) on to a reference filter wheel 19. The reference wheel contains a plurality of optical filters (not shown), at least one of which has a narrow bandpass centred on 589.6 (sodium 'D' lines). This is referred to as yellow the filter and transmits light produced by sodium atoms in the flame to pass through collimating lens 20 which redirects divergent rays on to photomultiplier tube 9.

The remaining filters in the filter wheel 19 are reference filters which are used to compensate for background chemical species such as carbon dioxide and water. Red filters were found to be suitable for this purpose because, nominally transmitting at 600 nm, they are (relatively) insensitive to NaCl emissions but sensitive to $CO_2$ and $H_2O$ emissions.

A beam stop (not shown) is also included to prevent paraxial rays from reaching the photomultiplier tube 9.

The photomultiplier tube 9 is maintained at a temperature of 13±0.1° C. by a forced air cooling thermoelectric (FACT) system (not shown).

During operation, rotation of filter wheel 19 causes modulation of the light reaching photomultiplier tube 9 via the filters. Filter wheel 19 also provides a reference signal by means of a pinhole which gives a peak of unfiltered light corresponding to one full revolution.

A phase sensitive a.c. amplifier (not shown) receives the output from the photomultiplier tube 9 and amplifies the reference signal and signals having related frequency and phase, namely the signals associated with the yellow and red filters (the yellow and red signals respectively).

These signals are measured in the presence of known concentrations of $CO_2$ and $H_2O$ but with salt absent. The relationship between the two can then be used to determine the background yellow signal (salt absent) from within the facemask where $CO_2$ and $H_2O$ are present. This information is then used to adjust the yellow signal obtained with salt present for background $CO_2$ and $H_2O$.

Figure 4A:
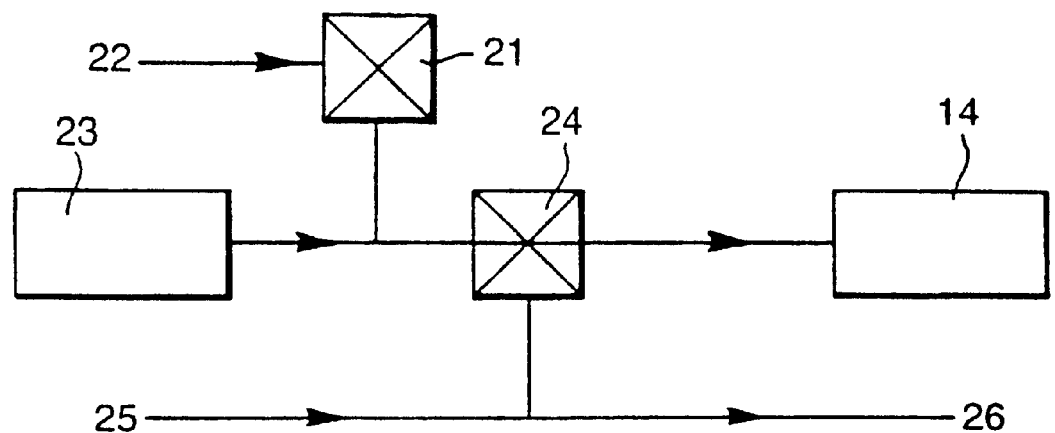
FIGS. 4a and 4b show a valve arrangement used to achieve pulsed sampling with the current invention.

Referring to FIG. 4a, during inhalation valve 21 is closed blocking clean air from input 22; sample air from respirator 23 is fed to photometer 14, at 2 l $min^{-1}$, via valve 24 and clean air (8 l/min) from input 25 is dumped via outlet 26.

Figure 4B:
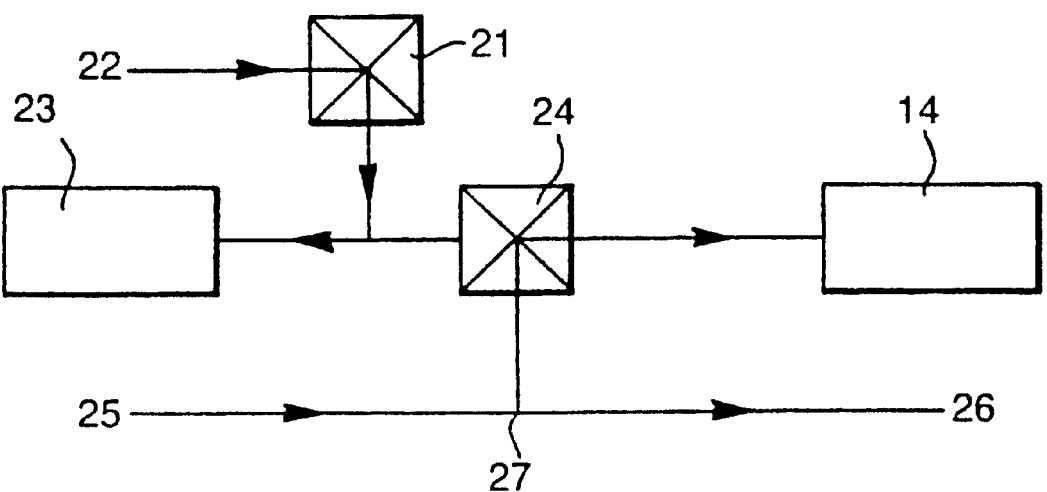

Referring to FIG. 4b, during exhalation valve 24 is switched such that 2 l $min^{-1}$ of air is supplied to the photometer 14 from input 25 via 'T'-piece 27. The remaining 6 l/min air from input 25 is dumped via outlet 26. At the same time, valve 21 is opened so that clean air from input 22 flows, at 1 l $min^{-1}$, to respirator 23. By the diversion of clean air into the respirator during exhalation, condensed water and residual salt is removed before the next sample is drawn.

Figure 5:
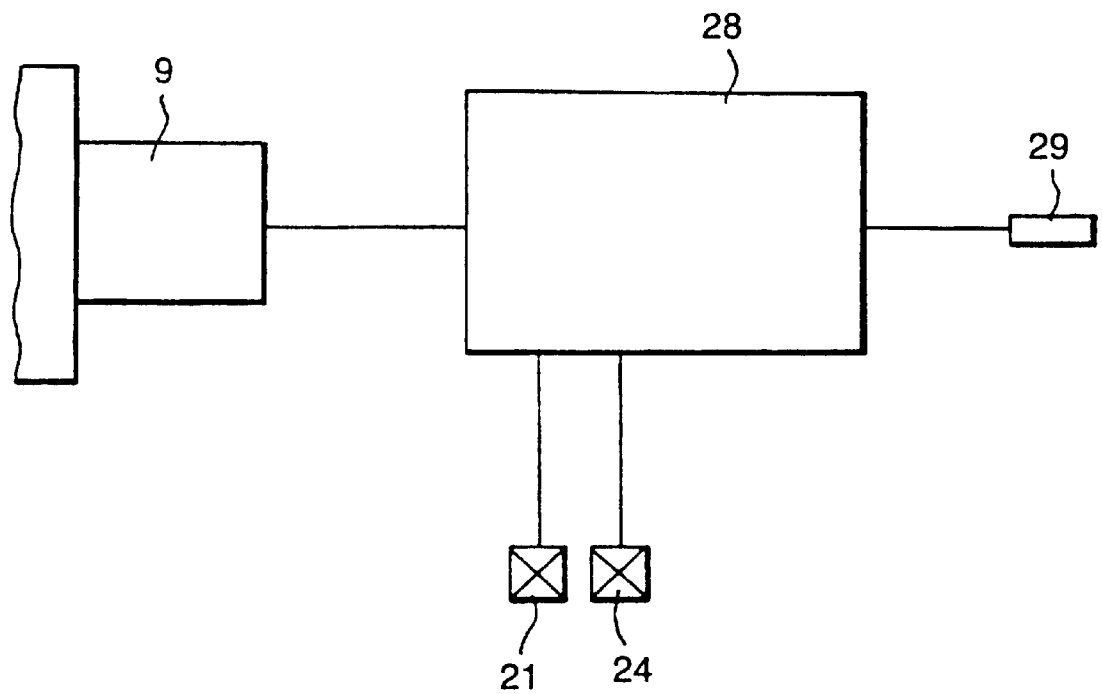
FIG. 5 shows the configuration of components used in the current invention.

Referring to FIG. 5, switching of valves 21 and 24 may be controlled by a computer 28 which identifies the inhalation and exhalation periods of the breathing cycle by pressure variations within the face mask measured by a micromanometer 29 located therein.

The computer 28 also analyses the output signal from photomultiplier 9 and, using the reference peak of unfiltered light as a marker, splits it into yellow (589.6 nm) and red (600 nm) signals.

Figure 6:
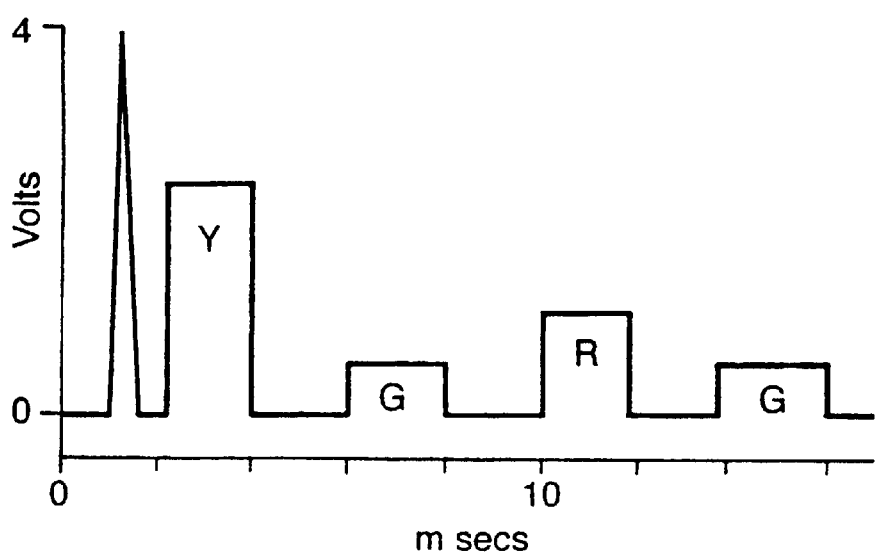
FIG. 6 shows (schematically) the output of a photomultiplier tube used in conjunction with a four position rotating filter wheel for a sample of clean air.

The output from a photomultiplier tube, as used in the current invention, for a sample of clean, compressed air, is shown in FIG. 6. A four position filter wheel, rotating at 66.66 Hz, and having a yellow filter, two green filters and a red filter was used. The regions of the graph associated with each of these filters are designated Y, G and R respectively.

From FIG. 6 it can be seen that the time window associated with each filter has a duration of about 2 milliseconds. The rate of data acquisition should be selected accordingly in order to record single particle events within this window. A DT2838 analogue to digital converter running on a 300 MHz pentium™ processor was used. This allowed data collection at a rate of 40 kHz, i.e. about 80 samples in each filter window.

The acquisition system used provides several data collection channels. In addition to the foregoing, two of these are used to monitor pressure inside the face mask and challenge salt concentration. The former is measured using a Furness Controls Micromanometer MCD FC001 and the latter is measured using a commercially available flame photometer. In order to collect raw data for retrospective analysis, about 3 Mbytes of storage space is required for a typical 5 minute experiment.

What is claimed is:

1. A flame photometer detector comprising:
   a flame chamber having a burner, a hydrogen inlet, a sample inlet and a window, transparent to radiation produced therein;
   means for detecting independently a first radiation and a second radiation, and producing corresponding electrical signals, wherein the intensity of the first radiation is dependent on the concentration in the flame chamber of at least one chemical species to be detected and of one or more background chemical species and the intensity of the second radiation is substantially independent of the concentration in the flame chamber of the chemical species to be detected and is dependent on the concentration in the flame chamber of the background chemicals species,
   means for modulating the first and second radiation, and wherein the detecting means is selective to radiation so modulated and
   data acquisition means for measuring the electrical signals and comparing the data so obtained with calibration data obtained in the presence of the background chemical species and the absence of the chemical species to be detected.

2. The detector of claim 1 where the data acquisition means is capable of acquiring data at a rate sufficient to record single particle events within the flame chamber.

3. The detector of claim 1 where the modulating means comprises one or more optical filters associated with each of the first and second radiation, the passband of each filter containing the wavelength of the associated radiation and the filters being mounted on a rotating wheel located in the path of the radiation.

4. The detector of claim 3 where the rotating wheel includes means for producing a reference signal and the means for measuring the electrical signal and comparing the data with calibration data includes a computer adapted to separate the various modulated electrical signals by reference to the reference signal and to effect the subsequent data processing.

5. The detector of claim 4 where the means for producing a reference signal comprises a pinhole which allows a pulse of unfiltered light corresponding to one revolution of the wheel to reach the means for detecting radiation.

6. A detector as claimed in claim 1 and further comprising means for directing radiation exiting the flame chamber on to the filters.

7. The detector of claim 6 and further comprising means for directing modulated radiation towards the means for detecting radiation.

8. The detector of claim 7 where the detecting means comprises a photomultiplier tube.

9. A detector as claimed in claim 1 for use in testing the efficiency of respirator facemasks, further comprising means for directing sample air from the interior of a facemask to the flame chamber during inhalation by a subject wearing said facemask.

10. A detector as claimed in claim 9 where the means for directing sample air comprises a valve, adapted for switching airflow from the interior of the facemask between the flame chamber and an outlet; a manometer for measuring pressure within the facemask and means for operating one or more valves in response to pressure variations measured by the manometer.

11. The detector of claim 10 and further comprising a valve for switching airflow from an inlet through the facemask during exhalation.

12. The detector of claim 1 where th e chemical species to be detected is a sodium salt, the background chemical species include $CO_2$ and $H_2O$ the first radiation has a wavelength of about 589.6 nm and the second radiation has a wavelength of about 600 nm.

13. The detector of claim 1 adapted for measuring the penetration of a respirator by a chemical species and further including means for directing sample air to the flame chamber during inhalation and directing fresh air to the flame chamber and to the respirator during exhalation.

14. A method of measuring the presence of a chemical species using a flame photometer detector including the steps of:
   i) directing sample air to the flame chamber during inhalation and directing fresh air to the flame chamber and to the respirator during exhalation;
   ii) measuring a first radiation and a second radiation, and producing corresponding electrical signals, wherein the intensity of the first radiation is dependent on the concentration in the flame chamber of the chemical species to be detected and of one or more background chemical species and the intensity of the second radiation is substantially independent of the concentration in the flame chamber of the chemical species to be detected and is dependent on the concentration in the flame chamber of the background chemicals species; and
   iii) comparing the data so obtained with calibration data obtained in the presence of the background chemical species and the absence of the chemical species to be detected.

15. A flame photometer detector comprising:
   a flame chamber having a burner, a hydrogen inlet, a sample inlet and a window, transparent to radiation produced therein;
   means for detecting independently a first radiation and a second radiation, and producing corresponding electrical signals, wherein the intensity of the first radiation is dependent on the concentration in the flame chamber of at least one chemical species to be detected and of one or more background chemical species and the intensity of the second radiation is substantially independent of the concentration in the flame chamber of the chemical species to be detected and is dependent on the concentration in the flame chamber of the background chemicals species, and data acquisition means for measuring the electrical signals and comparing the data so obtained with calibration data obtained in the presence of the background chemical species and the absence of the chemical species to be detected, where the data acquisition means is capable of acquiring data at a rate sufficient to record single particle events within the flame chamber.

* * * * *